Figure 1A:
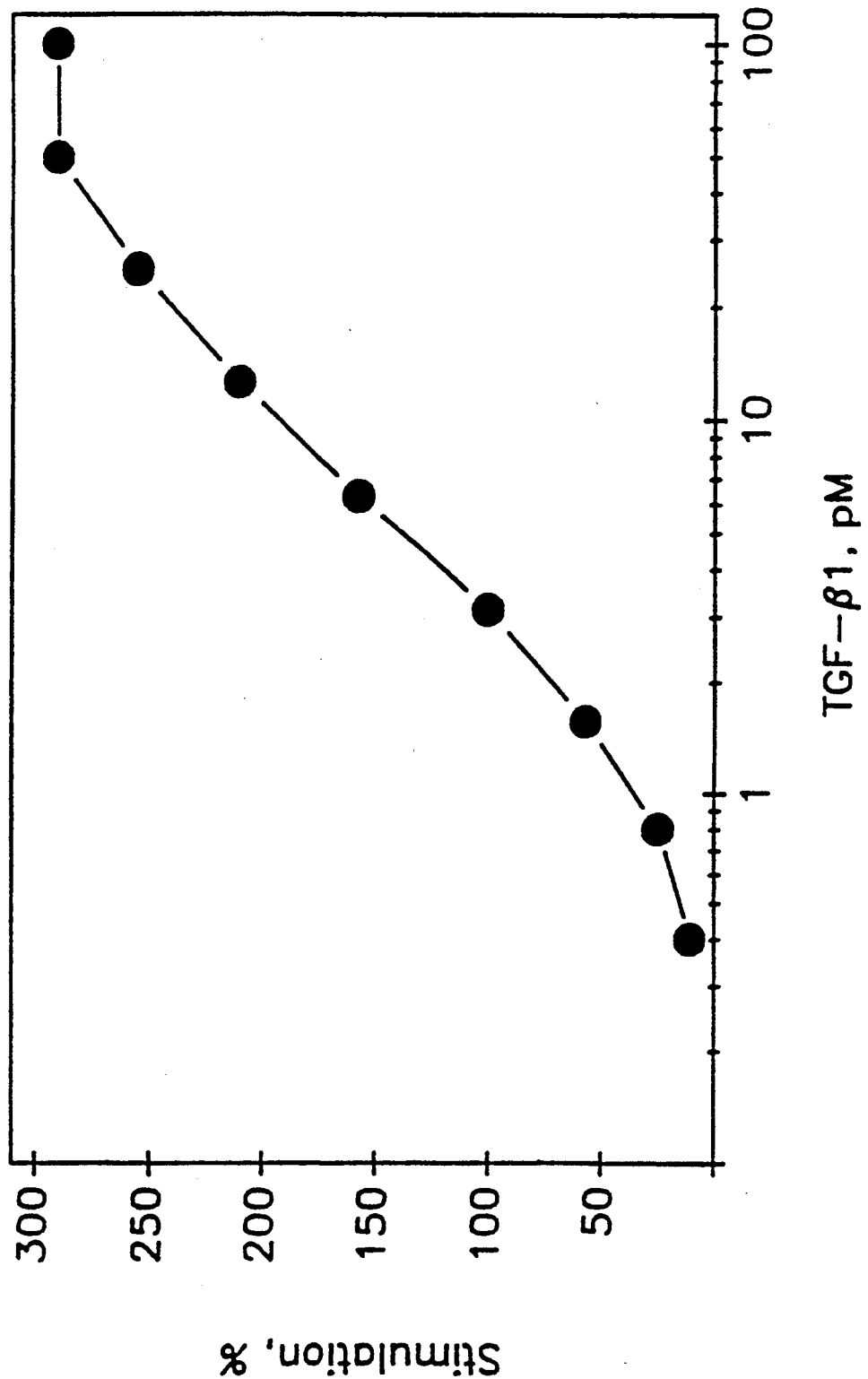

United States Patent [19]

Lioubin et al.

[11] Patent Number: 5,340,925
[45] Date of Patent: Aug. 23, 1994

[54] NORMAL HUMAN GROWTH REGULATORY RECEPTOR FOR TGF-β

[75] Inventors: Mario N. Lioubin, Bellevue; Thomas J. Brown; Anthony F. Purchio, both of Seattle, all of Wash.

[73] Assignee: Oncogen, Seattle, Wash.

[21] Appl. No.: 900,511

[22] Filed: Jun. 17, 1992

Related U.S. Application Data

[63] Continuation of Ser. No. 269,524, Nov. 14, 1988, abandoned.

[51] Int. Cl.$^5$ ............................................. C07K 15/00
[52] U.S. Cl. .................................. 530/395; 530/399; 530/413; 530/350
[58] Field of Search ............... 530/350, 395, 399, 413; 435/69.1

[56] References Cited

U.S. PATENT DOCUMENTS 4,286,690  9/1981  Pastka ................................ 530/351

OTHER PUBLICATIONS

Massague et al., J. Cell. Physiol. Suppl. 5:43–47 (1987).
Massague and Like, J. Biol. Chem. 260(5):2636–2645 (1985).
Massague, J. Biol. Chem. 260(11):7059–7066 (1985).
Fanger et al., Biochemistry 25:3083–3091 (1986).
Fanger and Sporn, Analytical Biochem. 156:444–453 (1986).
Chiefetz et al., Cell 48:409–415 (1987).
Segarini et al., J. Biol. Chem. 263(17):8366–8370 (1988).
Massague (1985) J. Biol. Chem. 260(11), 7059–7066.
Massague et al. (1985) J. Biol. Chem. 260(5), 2636–2645.
Segarini et al. (1988) J. Biol. Chem. 263(17), 8366–8370.
Herzberg et al. (1985) Biochem. Biophys. Res. Comm. 129, 789–796.
Pharmacia Fine Chemicals "Affinity Chromatography" pp. 6–10 (1983).
Sofer et al. (1983) BioTechniques Nov./Dec., 198–203.

*Primary Examiner*—R. Keith Baker
*Attorney, Agent, or Firm*—Pennie & Edmonds

[57] ABSTRACT

Type III TGF-β receptor is identified in and purified from normal human embryonic palatal mesenchyme (HEPM) cells and the purified product characterized structurally and functionally. HEPM cells were found to express high levels of the type III TGF-β receptor and were found to significantly down-regulate two classes of TGF-β receptor binding site. Purification of the type III TGF-β receptor from solubilized HEPM cell membranes by affinity chromatography yielded a biologically active protein of about 205 kd which specifically binds both the recombinant and natural forms of TGF-β1 and TGF-β2, with affinity dissociation constants in the picomolar range.

15 Claims, 13 Drawing Sheets

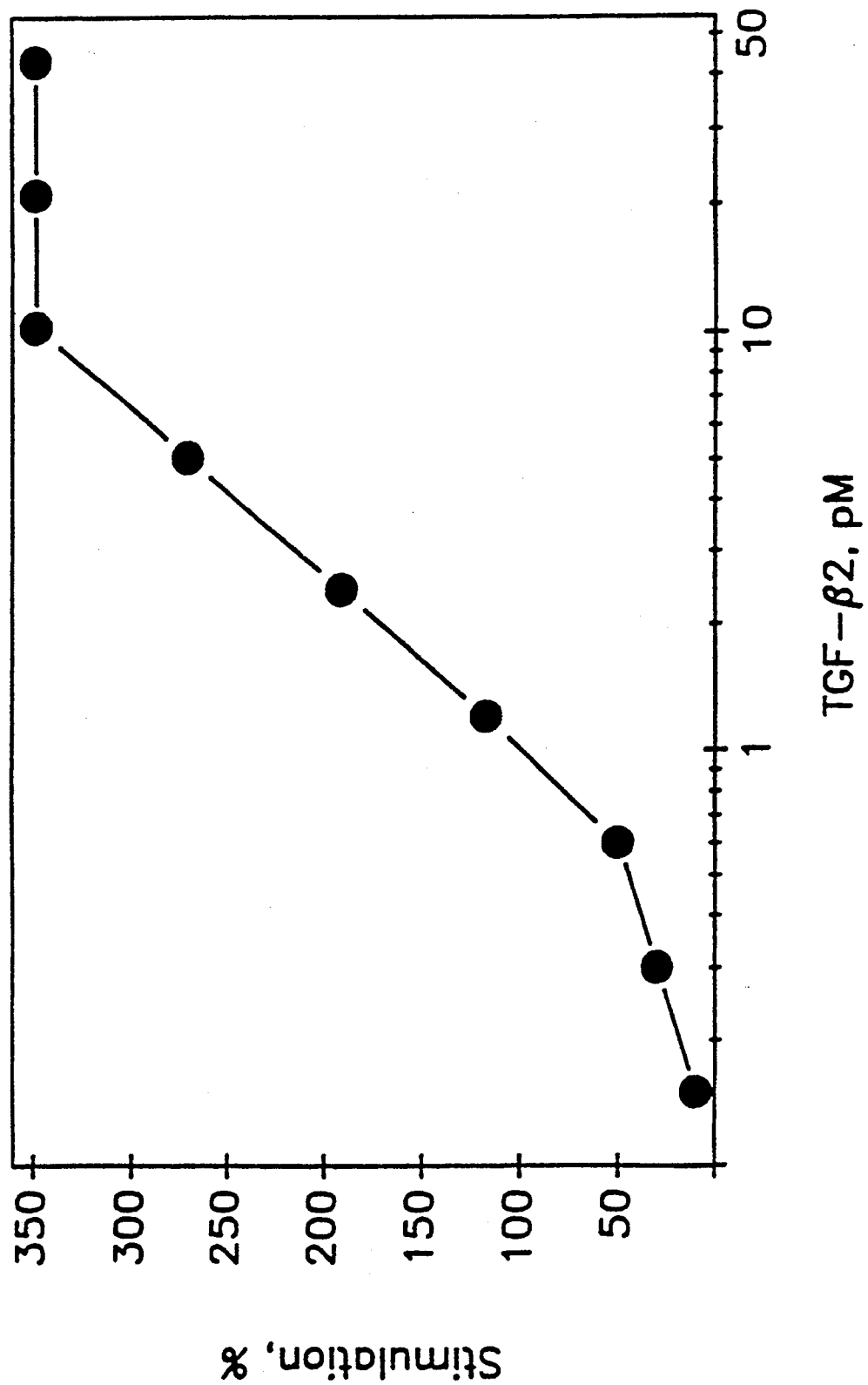

NORMAL HUMAN GROWTH REGULATORY RECEPTOR FOR TGF-β

This is a continuation of application Ser. No. 07/269,524, filed Nov. 14, 1988, now abandoned.

TABLE OF CONTENTS

1. Introduction
2. Background Of The Invention
   2.1. TGF-β
   2.2. TGF-β Receptors
3. Summary Of The Invention
4. Brief Description Of The Invention
5. Detailed Description Of The Invention
   5.1. Identification Of The Normal Growth Regulatory Receptor For TGF-β
   5.2. Purification Of Type III TGF-β Receptor
   5.3. Production Of The Type III TGF-β Receptor
   5.4. Molecular Cloning and Expression Of Type III TGF-β Receptor Gene
      5.4.1. Construction Of Expression Vectors Containing The Type III TGF-β Receptor Coding Sequence
      5.4.2. Identification Of Transfectants Or Transformants Expressing The Type III TGF-β Receptor Gene Product
6. Example: Identification And Characterization of the TGF-β Receptor on HEPM Cells
   6.1. Materials and Methods
      6.1.1. Growth Stimulation Assays
      6.1.2. Stimulation Of Anchorage Independent Growth Assay
      6.1.3. Co-Stimulation With EGF Assay
      6.1.4. Radioreceptor Assay
      6.1.5. Affinity Labeling of TGF-β Cell Surface Receptors
   6.2. Biological Response Mediated by the TGF-β Receptor
      6.2.1. Proliferative Response
      6.2.2. Synergism of EGF in the TGFβ/TGF-β Receptor System
   6.3. Properties of HEPM Cell-Surface Receptors for TGF-β
      6.3.1. Determination of Receptor Number and Affinity
      6.3.2. Relationship Between Receptor Occupancy And Biological Response
      6.3.3. Identification of TGF-β Receptors on HEPM Cells: Predominance of Type III Receptors
7. Example: Purification of Type III TGF-β Receptor
   7.1. Materials and Methods
      7.1.1. Preparation and Solubilization of Membranes
      7.1.2. Immobilization of TGF-β to Solid Support
      7.1.3. Affinity Labeling of Soluble TGF-β Receptors
      7.1.4. SDS-PAGE and Autoradiography
      7.1.5. Affinity Chromatography
   7.2. Characterization of Affinity Purified Type III TGF-β Receptor
      7.2.1. Electrophoretic Analysis
      7.2.2. Binding Capacity
      7.2.3. Amino Acid Composition and Sequencing

1. INTRODUCTION

The present invention relates to the production of purified type III TGF-β receptor. The purified TGF-β receptor of the invention is capable of binding both TGF-β1 and TGF-β2 and has been characterized biologically and structurally.

2. BACKGROUND OF THE INVENTION

2.1. TGF-β

Transforming growth factor-Beta (TGF-β) is a member of a recently described family of polypeptides that regulate cellular differentiation and proliferation. Other members of this family include Mullerian inhibitory substance (Cate et al., 1986, Cell 45:685–698), the inhibins (Mason et al., 1985, Nature 318:659–663) and a protein predicted from a transcript of the decapentaplegic gene complex of Drosophila (Padgett et al., 1987, Nature 325:81–84).

Four types of TGF-β have been identified and designated TGF-1, TGF-β2, TGF-β1.2, and TGF-β3. The first described type, TGF-β1, consists of two identical disulfide linked subunits having molecular weights of 13,000 (Assoian et al., 1983, J. Biol. Chem. 258:7155–7160; Frolik et al, 1983, Proc. Natl. Acad. Sci. USA 80:3676–3680; Frolik et al., 1984, J. Biol. Chem. 260:10995–11000). It has been purified from several tissue sources including placenta (Frolik et al., 1983, Nature 325:81–84), blood platelets (Childs et al., 1982, Proc. Natl. Acad. Sci. USA 79:5312–5316; Assoian et al., 1983, J. Biol. Chem. 258:7155–7160) kidney (Roberts et al., 1983, Biochemistry 22:5692–5698), and demineralized bone (Seyedin et al., 1985, Proc. Natl. Acad. Sci. USA 82:119–123). cDNA clones coding for human (Derynck et al., 1985, Nature 316:701–705), mouse (Derynck et al., 1986, J. Biol. Chem. 261:4377–4379) and simian (Sharples et al., 1987, DNA 6:239–244) TGF-β1 have been isolated DNA sequence analysis of these clones indicates that TGF-β1, is synthesized as a large precursor polypeptide, the carboxy terminus of which is cleaved to yield the mature TGF-β monomer. Strong sequence homology has been found throughout the TGF-β1, precursor protein from all of the above sources.

In the presence of 10% serum and epidermal growth factor, TGF-β1, promotes the anchorage independent growth of normal rat kidney fibroblasts (Roberts et al., 1981, Proc. Natl. Acad Sci USA 78:5339–5343; Roberts et al , 1982, Nature 295:417–419; Twardzik et al., 1985, J. Cell. Biochem. 28:289–297); in the presence of 10% serum alone, it is able to induce colony formation of AKR-2B fibroblasts (Tucker et al., 1983, Cancer Res. 43:1518–1586). TGF-β1, has also been shown to cause fetal rat muscle mesenchymal cells to differentiate and produce cartilage specific macromolecules (Seyedin et al., 1986, J. Biol. Chem. 261:5693–5695).

In contrast to its effect on cell proliferation, TGF-β1, purified from human platelets has been shown to inhibit the growth of certain cells in culture (Tucker et al., 1984 Science 226:705–707) TGF-β1 has also been shown to inhibit the growth of several human cancer cell lines (Roberts et al , 1985, Proc Natl Acad Sci. USA 82:119–123). This inhibitory/stimulatory effect of TGF-β1, may depend on several factors including cell type and the physiological state of the cells (for review see Sporn et al., 1986, Science 233:532–534).

TGF-β2, like TGF-β1, is a polypeptide of molecular weight 26,000 composed of two identical 13,000 dalton subunits which are disulfide linked (Chiefetz et al., 1987, Cell 48:409–415; Ikeda et al., 1987, Biochemistry 26:2406–2410) and has been isolated from bovine demineralized bone (Seydin et al., 1987, J. Biol. Chem. 262:1946–1949), porcine platelets (Cheifetz et al., 1987, 48:409–415), a human prostatic adenocarcinoma cell line, PC-3 (Ikeda et al., 1987, Biochemistry 26:2406–2410), and a human gliablastoma cell line (Wrann et al., 1987, EMBO 6:1633–1636). cDNA clones coding for human and simian TGF-$\beta$2 have been isolated (Madisen et al., 1988, DNA 7:1–8; Webb et al., 1988, DNA 7:493–497). The mature TGF-$\beta$2 monomer is cleaved from one of two larger precursor polypeptides, the mRNAs of which may arise via differential splicing (Webb et al., 1988, DNA 7:493–497).

TGF-$\beta$1and TGF-$\beta$2 share 71% amino acid sequence identity in their mature regions, and 41% identity in their precursor structures. TGF-$\beta$3, the amino acid sequence of which has very recently been deduced from cDNA clones, appears to contain a C-terminal 112 amino acid sequence with about 80% homology to the mature monomers of TGF-$\beta$1, and TGF-$\beta$2 (Dijke et al., 1988, Proc. Natl. Acad. Sci. USA 85:4715–4719). TGF-$\beta$1.2 is a heterodimeric form comprising a $\beta$1 and $\beta$2 subunit linked by disulfide bonds (Cheifetz et al., 1987, Cell 48:409–415).

2.2. TGF-$\beta$ RECEPTORS

Three types of TGF-$\beta$ receptors have been described and defined as types I, II and III on the basis of individual structural and functional properties. The type III receptor for TGF-$\beta$ is a large, disulfied-linked glycoprotein containing a 280–330 kilodalton subunit within which the ligand-binding site is located (Massague, 1985, J. Biol. Chem. 260:7059–7066). Although TGF-$\beta$1, and TGF-$\beta$2 bind differentially to the type I and type II receptors, the type III receptor exhibits similar affinity for both ligands (Cheifetz et al., 1987, Cell 48:409–415).

Occupancy of type III receptors has been implicated in the mediation of several cellular responses to both TGF-$\beta$1, and TGF-$\beta$2 including the stimulation of fibronectin (Ignotz and Massague, 1986, J. Biol. Chem. 61:4337–4345), type I collagen (Roberts et al., 1986, Proc. Natl. Acad. Sci. USA 83:4167–4171), cell adhesion receptor synthesis and expression (Ignotz and Massague, 1987, Cell 51:189–197) and chondroitin/dermatan sulfate proteoglycans (Bassols and Massague, 1988, J. Biol. Chem. 263:3039–3045). The type III receptor may play a pivotal role in mediating changes in the extracellular matrix and cell adhesion properties induced by TGF-$\beta$, resulting in the induction or repression of certain cell phenotypes and cell proliferation, i.e., induced proliferation of fibroblasts in semi-solid medium (Assoian et al., 1983, J. Biol. Chem. 258:7155–7160); inhibition of the proliferation of epithelial cells (Roberts et al., 1985, Proc. Natl. Acad. Sci. USA 82:119–123), T and B lymphocytes (Kehrl et al., 1986, J. Exp. Med. 163:1037–1050; Kehrl et al., 1985, Clin. Res. 33:610–615), thymocytes (Ristow, 1986, Proc. Natl. Acad. Sci. USA 83:5531–5533), and certain tumor cells (Roberts et al., 1985, Proc. Natl. Acad. Sci. USA 82:119–123); stimulation of chondrogenesis (Seyedin et al., 1985, Proc. Natl. Acad. Sci. USA 82:2267–2271), osteogenesis (Centrella et al., 1986, Endocrinology 19:2306–2312) and epithelial cell differentiation (Masui et al., 1986, Proc. Natl. Acad. Sci. USA 83:2438–2442); and inhibition of expression of adipose (Ignotz et al., 1985, Proc. Natl. Acad. Sci. USA 82:8530–8534), skeletal muscle (Olson et al., 1986, J. Cell. Biol. 103:1799–1805) and hematopoietic (Ohta et al., 1987, Nature 329:539–541) phenotypes, High affinity receptors for TGF-$\beta$ have been found on nearly all cells examined to date, including cells of epithelial, mesenchymal, and hematopoeitic origin, on both normal and tumor cells, cells of adult or embryonic origin, and cells from different species (Wakefield et al., 1987, J. Cell. Biol. 105:965).

Biologically latent TGF-$\beta$ is unable to bind to its receptor or generate a biological response, indicating that activation of TGF-$\beta$ is required before the TGF-$\beta$ receptor will recognize and bind its ligand (Wakefield et al., 1987, J. Cell Biol. 105:965). Neither the mechanisms behind TGF-$\beta$ activation nor the reasons for the inability of TGF-$\beta$ receptor to recognize and bind latent TGF-$\beta$ are understood.

Results from a variety of studies involving the TGF-$\beta$s and their receptors have raised interesting questions regarding the role of the TGF-$\beta$ system in tumorigenesis. Although TGF-$\beta$ receptors appear to be universally expressed on all cell types, some notable exceptions have been found; for example, most retinoblastoma cell lines appear not to have functional TGF-$\beta$ receptors, the absence of which may allow these cells to escape the otherwise normal growth-controlling actions of TGF-$\beta$ (Kimichi et al., 1988, Science 240:196–199). In this regard, the expression or loss of expression of factors which regulate the synthesis and/or expression of the TGF-$\beta$ receptor may lead to a concomitant loss of responsiveness to the growth restraining effect of TGF-$\beta$. Another mechanism by which tumor cells may lose their ability to respond to and be regulated by TGF-$\beta$ may involve a cells inability to activate the latent form of TGF-$\beta$, thereby blocking the growth inhibitory signal generated by ligand-receptor binding. (Wakefield, 1987, J. Cell. Biol. 105:965–975).

A role for TGF-$\beta$ and its receptor in early mammalian development has been suggested. Critical structures involved in the morphogenesis of early mouse embryos have shown specific immunohistochemical localization of TGF-$\beta$ (Heine et al., 1987, Proc. Am. Assoc. Cancer Res. 28:53). TGF-$\beta$ exhibits either a growth promoting or growth inhibiting effect on cultured normal fetal fibroblasts, depending on the gestational age of the fetus of origin, suggesting that a maturational change in the biology of TGF-$\beta$ may occur between 13 and 16 weeks into human gestation (Hill et al., 1986, 128:322–328). In addition, murine embryonal carcinoma cells which appear to have few, if any, receptors for TGF-$\beta$, express receptors and become sensitive to the anti-proliferative action of TGF-$\beta$ after being induced to differentiate into a extraembryonic endoderm-like cells, suggesting that TGF-$\beta$ receptors may begin to appear on embryonic cells following commitment to a specific differentiation pathway (Rizzino, 1987, Cancer Res. 47:4386–4390). A role for TGF-$\beta$ in early development is also supported by the discovery that a drosophila gene involved in pattern formation encodes a protein having significant primary sequence homology with TGF-$\beta$.

The TGF-$\beta$ family of growth regulatory factors appears to play an essential role in the control of cell growth and differentiation in organisms ranging from drosophila to man. Although three members of the TGF-$\beta$ gene family have now been identified and cloned, very little is known about the specific mechanisms associated with the numerous receptor-mediated actions of TGF-$\beta$. Current knowledge regarding the undoubtedly complex biology of the TGF-$\beta$ system therefore remains confined, and further progress depends on a better understanding of TGF-$\beta$ receptor molecular biology.

3. SUMMARY OF THE INVENTION

The present invention is related to purified type III TGF-$\beta$ receptor and methods for its production. The purification of the type III TGF-$\beta$ receptor has enabled applicants to determine part of its amino acid sequence, thereby making possible the use of molecular cloning technologies to produce large quantities of TGF-$\beta$ receptor.

The invention provides, for the first time, a powerful research tool essential to uncovering the molecular mechanisms associated with the variety of effects the TGF-$\beta$s have on cell growth and differentiation.

Purified type III TGF-$\beta$ receptor may find uses in developing methods for the control of cell-growth and may contribute significantly to research aimed at explaining the molecular biology of cell-growth processes.

4. BRIEF DESCRIPTION OF THE FIGURES

FIGS. 1(A) and 1(B) Bioactivity of TGF-$\beta$ on HEPM cells: incorporation of radionuclide into DNA. Results are presented as percent stimulation vs the picomolar (pM) concentration of TGF-$\beta$. Percent stimulation was calculated as follows: treated (cpm)-untreated (cpm)/untreated (cpm) x 100. Panel A: TGF-$\beta$1, treatment. Panel B: TGF-$\beta$2 treatment.

Figure 2:
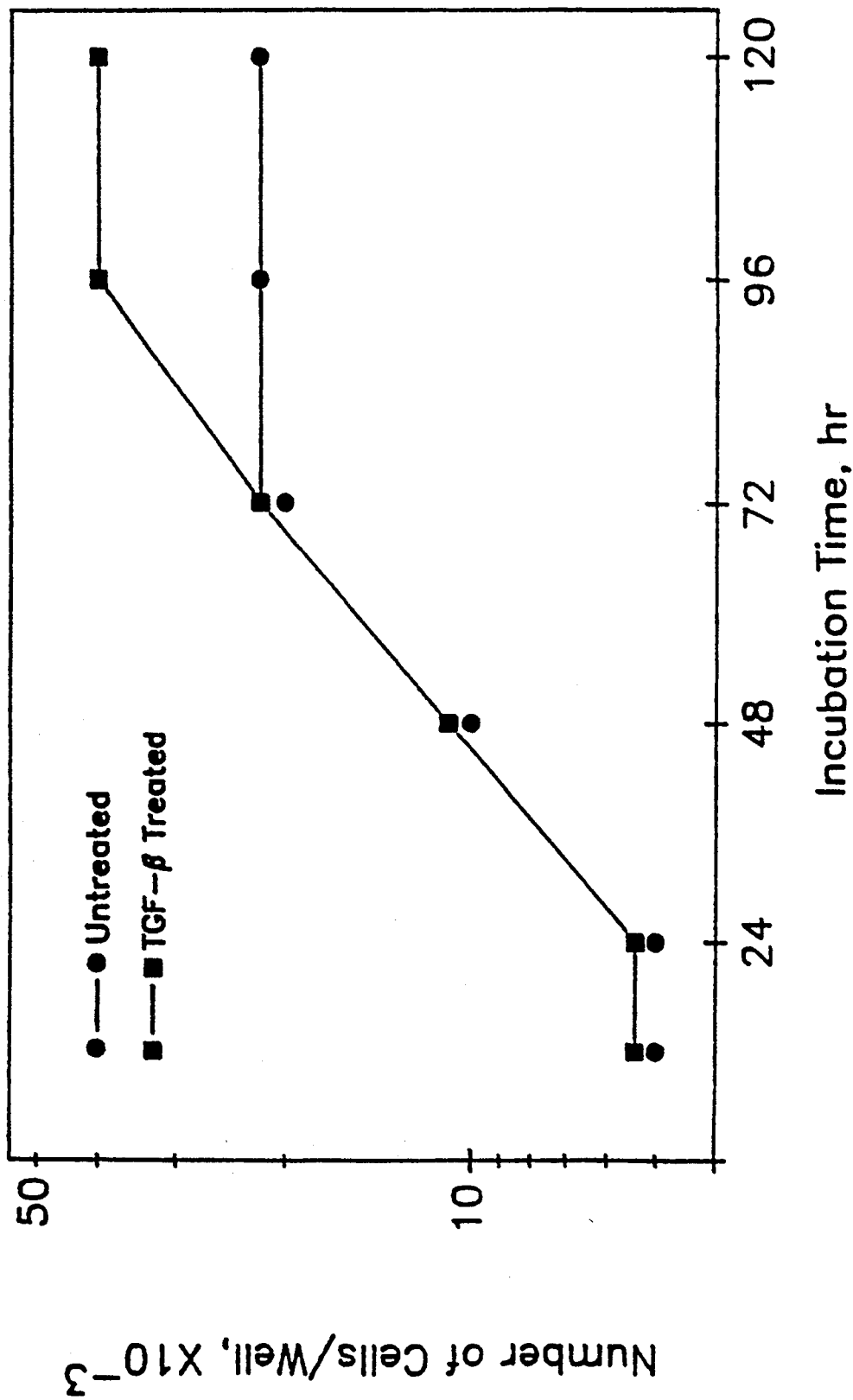

FIG. 2 Bioactivity of TGF-$\beta$ on HEPM cells: cell proliferation. Cell counts were taken at 24 hour intervals until 120 hours post treatment. The data is presented as the number of cells per well vs incubation time (hours). By 96 hours, cultures treated with 50 pM TGF-$\beta$1, (■) had reached a cell density twice that of untreated cultures (●).

Figure 3A:
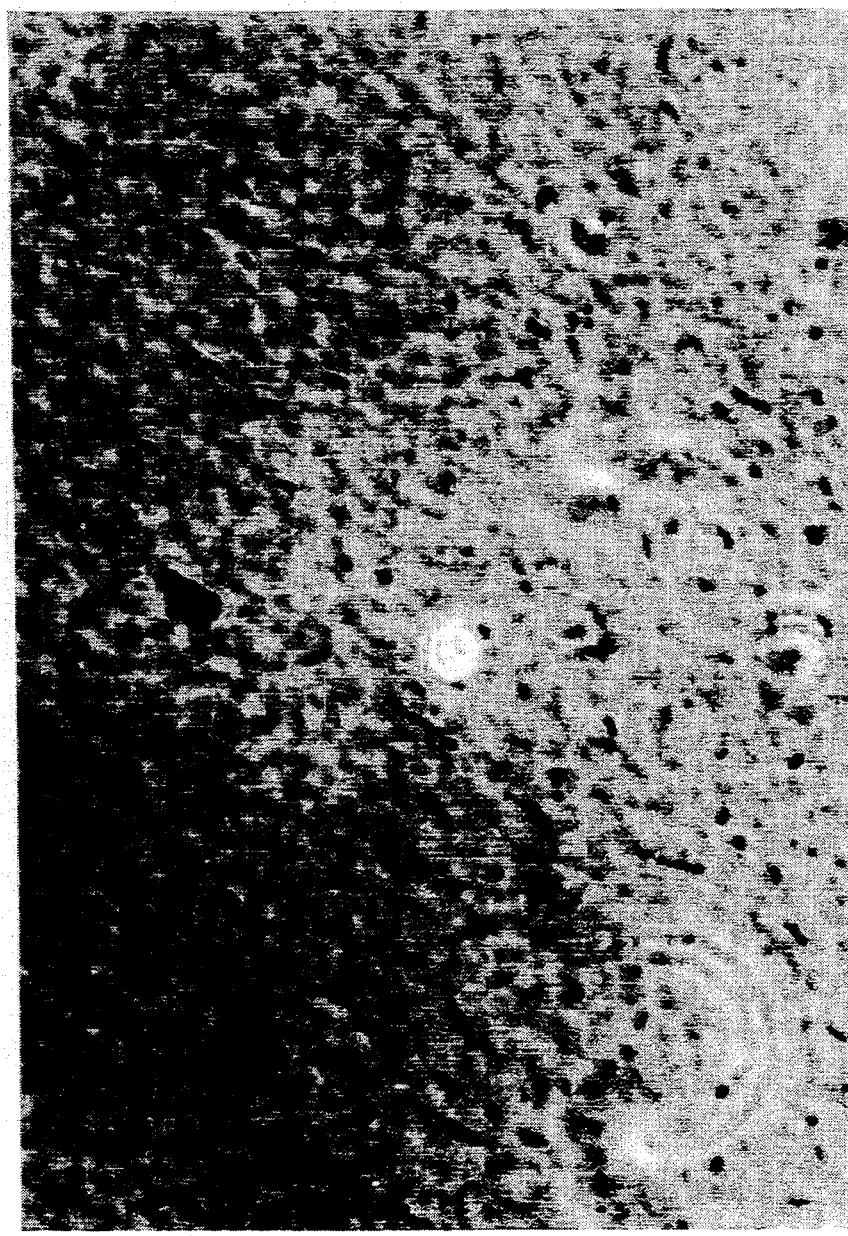
Figure 3B:

FIGS. 3(A) and 3(B) Bioactivity of TGF-$\beta$ on HEPM cells: stimulation of growth in soft agar. Cells were treated with 50 pM TGF-$\beta$1, at the time of plating and colony formation was enumerated on day 13. Panel A: untreated cells Panel B: TGF-$\beta$1, treated cells Wells containing TGF-$\beta$1, had a mean colony number of 8±1.

Figure 4A:
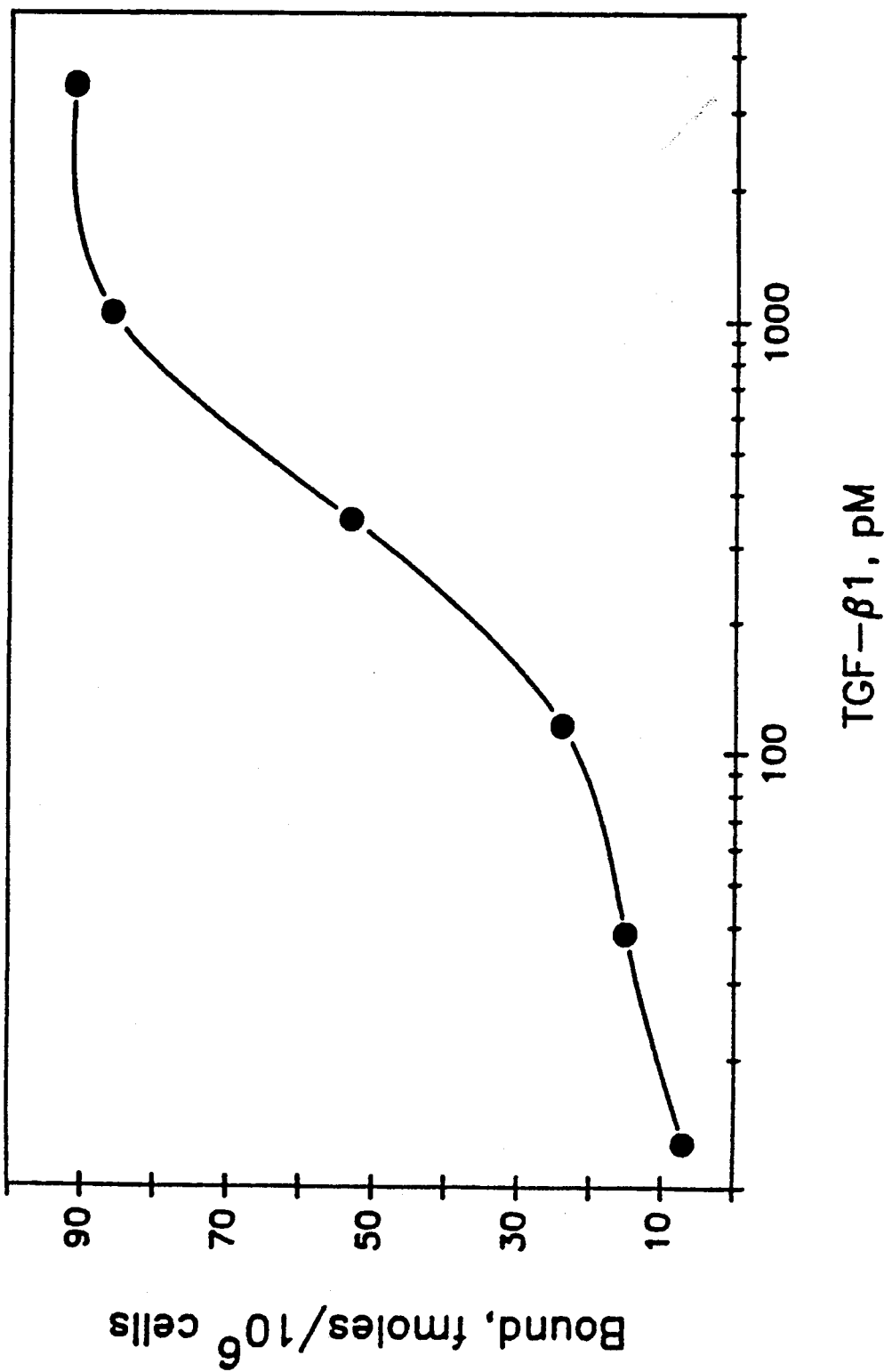
Figure 4B:
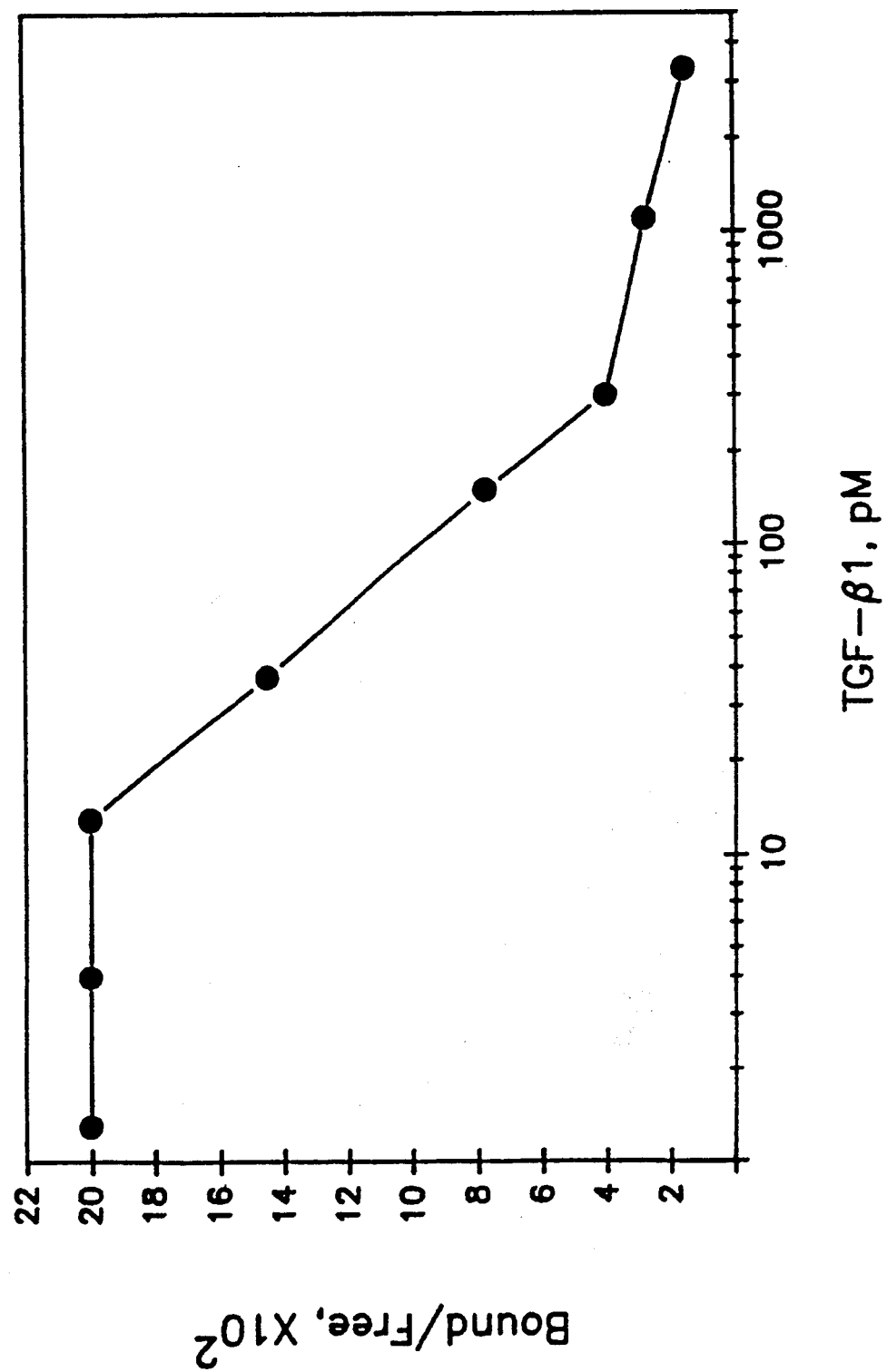

FIGS. 4(A) and 4(B) Binding of [$^{125}$I]-iodo-TGF-$\beta$1 in competition with increasing amounts of unlabeled TGF-$\beta$1. The binding of radiolabeled TGF-$\beta$1, was saturable (FIG. 4A) and competed by unlabeled ligand (FIG. 4B); specific binding was 20% of total radioligand present.

Figure 5:
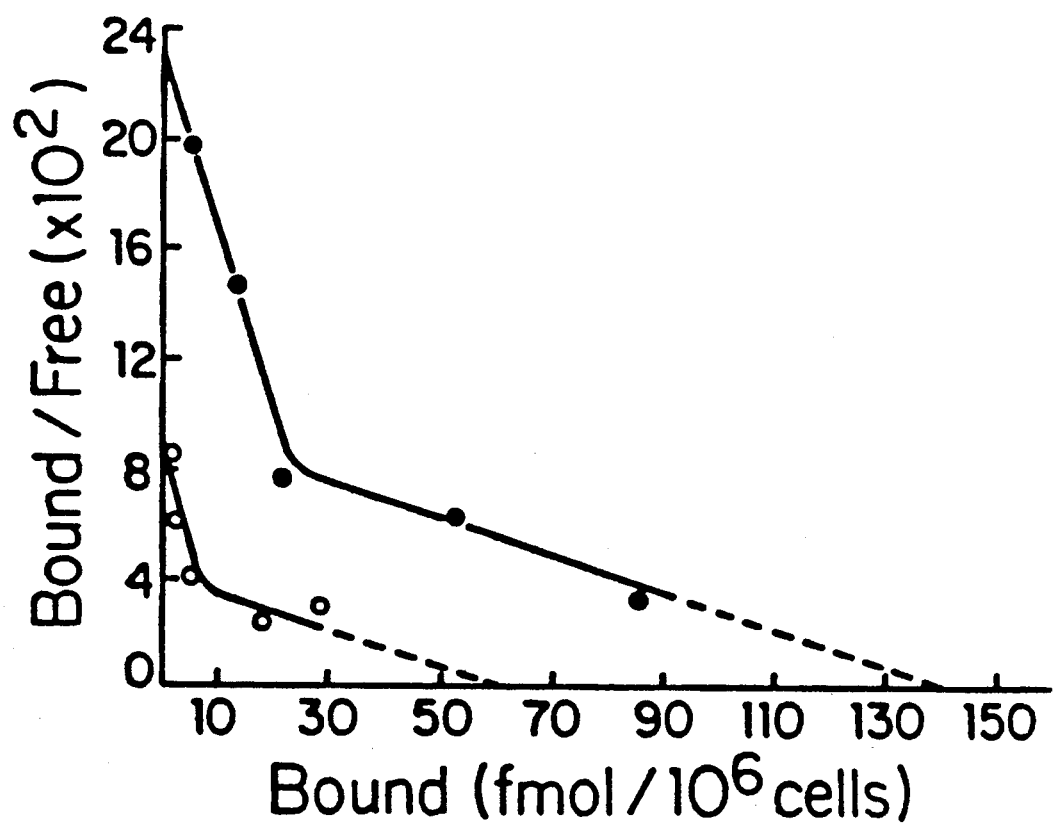

FIG. 5 Scatchard plot of competitive binding data (O) cells treated for 18 hours with 100 pM rTGF-$\beta$1, (●) untreated cells. The curvilinear isotherms obtained indicate the presence of at least two classes of TGF-$\beta$ binding sites. The parallelism seen between the isotherms indicates that down-regulation of the receptor occurs when cells are exposed to rTGF-$\beta$1, prior to binding.

Figure 6:
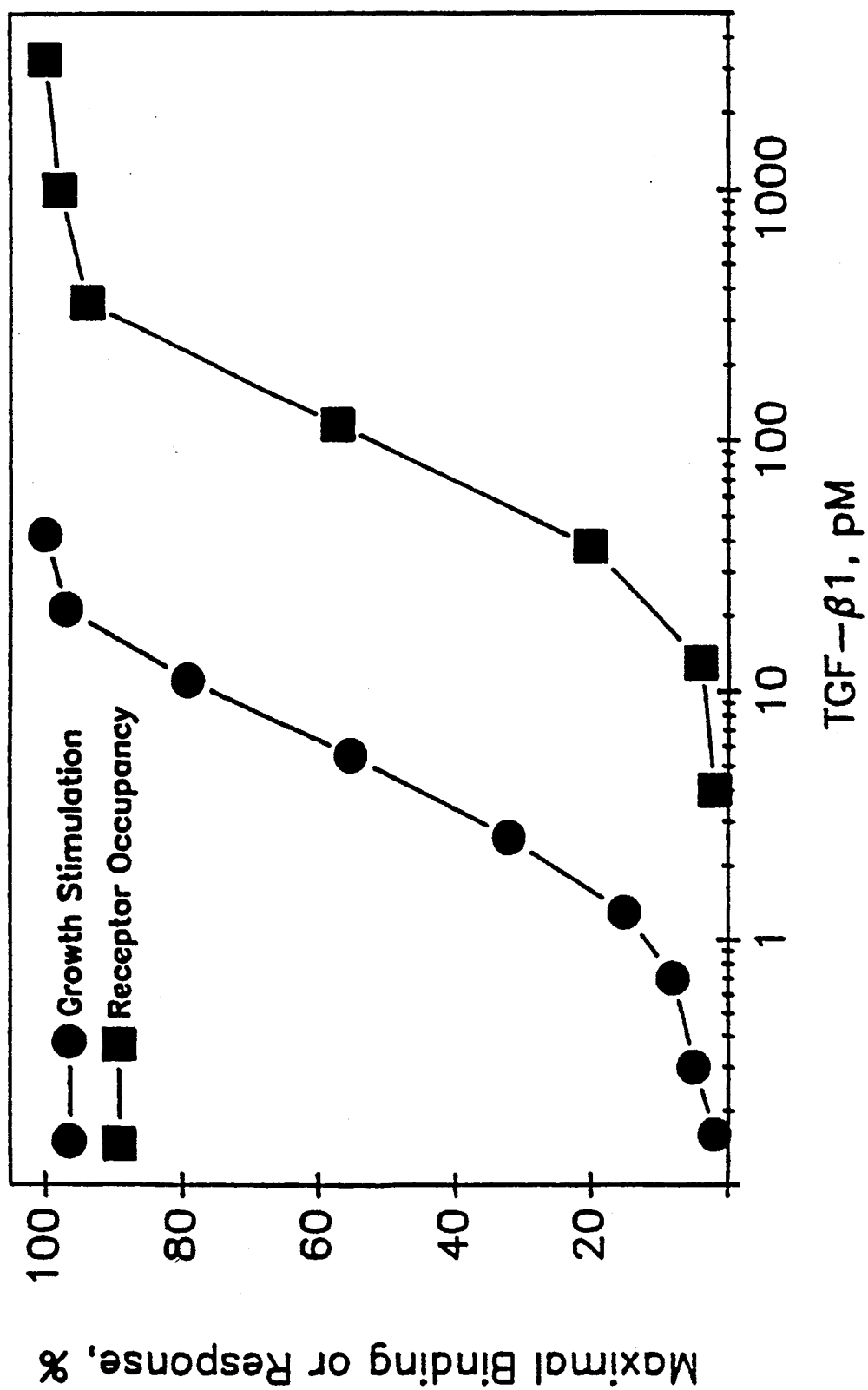

FIG. 6 Comparison of biological responses and receptor occupancy. The results are presented as percent maximal binding, or response, vs concentration of TGB-$\beta$1. Half-maximal growth stimulation (●) occurred at 5 pM TGF-$\beta$1, while half-maximal receptor occupancy (■) occured at 100 pM TGF-$\beta$1. Thus, full biological response is obtained when only 20% of the receptors are occupied with TGF-$\beta$1, FIG. 7 Autoradiography of cell surface affinity labeled TGF-$\beta$ receptor, two day exposure. Samples were incubated with [$^{125}$I]-iodo-TGF-$\beta$1 or [$^{125}$I]-iodo-TGF-$\beta$2 alone or in the presence of 1,000 ng unlabeled TGF-$\beta$1, or TGF-$\beta$2. Lane 1: labeled TGF-$\beta$1; lane 2: labeled TGF-$\beta$1,+unlabeled TGF-$\beta$1, ; lane 3: labeled TGF-$\beta$1,+unlabeled TGF-$\beta$2; lane 4: labeled TGF-$\beta$2; lane 5: labeled TGF-$\beta$2+unlabeled TGF-$\beta$1; lane 6: labeled TGF-$\beta$2+unlabeled TGF-$\beta$2.

Figure 8:
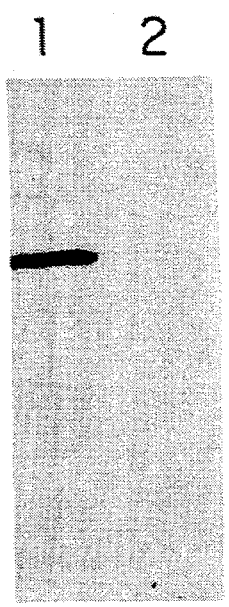

FIG. 8 Efficiency of coupling TGF-$\beta$1, to Affi-Gel resin. Aliquots of 5 $\mu$l solution before (lane 1) and after (lane 2) coupling, electrophoretically analyzed on 15% SDS-polyacrylamide gel with a 5% stacking gel in the absence of 2-mercaptoethanol. Coomassie staining revealed no detectable amounts of TGF-$\beta$ in lane 2 indicating a coupling efficiency of better than 90%.

Figure 9:
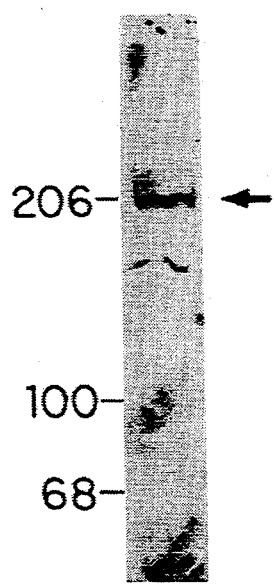

FIG. 9 Mobility of purified TGF-$\beta$ receptor on 6.25% SDS-PAGE (5% stacking gel) under reducing conditions. Only one Coomassie-stainable band is visible (migrating close to the myosin marker) at a calculated molecular mass of 200–206 Kd.

Figure 10:
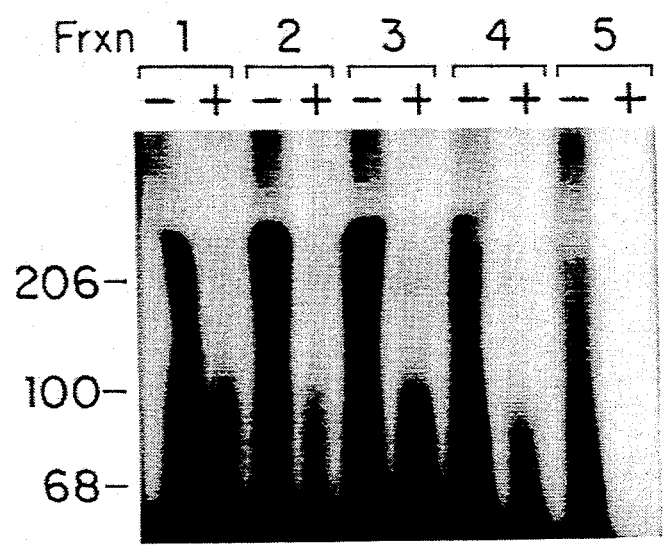

FIG. 10 Ability of purified TGF-$\beta$ receptor to bind TGF-$\beta$. Affinity purified receptor preparations were crosslinked to bound [$^{125}$I]-iodo-TGF-$\beta$ with DSS and analyzed on SDS-PAGE. Lanes marked (−) contained only [$^{125}$I]-iodo-TGF-$\beta$; lanes marked (+) contained [$^{125}$I]-iodo-TGF-$\beta$ in the presence of 1,000 ng/ml unlabeled TGF-$\beta$. The 240 Kd band is specifically labeled with radioligand and has the same mobility on SDS-PAGE as the receptor-TGF-$\beta$ complex from cell surface membranes (see FIG. 7).

5. DETAILED DESCRIPTION OF THE INVENTION

The present invention relates to the production of a purified receptor for transforming growth factor-beta (TGF-$\beta$). The purified TGF-$\beta$ receptor of the invention, a type III TGF-$\beta$ receptor, may be isolated from cells which naturally express such receptors on their surfaces. Alternatively, cells which have been transfected with expression vectors containing the type III TGF-$\beta$ receptor gene and which are capable of directing the synthesis of the mature, active receptor may be used as a source for isolating TGF-$\beta$ receptor.

The method of the invention is demonstrated herein, by way of examples, in which the type III TGF-$\beta$ receptor was identified and purified from HEPM cells, characterized, and used to obtain compositional and structural information. HEPM cells were found to express excessively high levels of type III TGF-$\beta$ receptors, making these cells an excellent source for the isolation and purification of this receptor. In a specific embodiment, type III TGF-$\beta$ receptor was purified to homogeneity by affinity chromatography. Specifically, recombinant TGF-$\beta$1 was immobilized onto polymeric resin and used to isolate type III TGF-$\beta$ receptor from a solution containing solubilized HEPM cell membranes. The affinity purified type III TGF-$\beta$ receptor isolated from HEPM cells has a molecular mass of about 200–206 kd and is capable of specifically binding TGF-$\beta$1, and TGF-$\beta$2. The amino acid composition and partial amino acid sequence of the type III TGF-$\beta$1, receptor was determined.

Purified type III TGF-$\beta$ receptor may find use in the treatment of a wide variety of cell-growth related disorders and, generally, as a means for controlling cell growth and differentiation. For example, purified type III TGF-$\beta$ receptor may be useful as a therapeutic scavenging agent in situations where constraining the activity of TGF-$\beta$ is desirable. In this regard, the use of the receptor as a scavenging agent could effectively inhibit binding of TGF-β to any of its natural target receptors, thereby blocking the cell proliferative or inhibitory signals generated by the ligand-receptor binding event. Since it appears that the vast majority of cell types are susceptible to TGF-β action, it may be useful to incorporate type III TGF-β receptors in drug delivery systems designed to localize the scavenging effect of the receptor to a certain population of cells, cell types, or specific tissues or organs. Antibodies to which the type III TGF-β receptors have been conjugated may be used to target scavenging activity to particular cells or groups of cells. In this regard, a wide variety of antibodies specific for individual cell types are known in the art and could be used in conjunction with the receptor to constrain TGF-β activity.

The ability to direct TGF-β into cells which are deficient in their ability to bind and respond to the growth modulatory activities of TGF-β may be desirable for the control of cell growth disorders. In this regard, type III TGF-β receptors conjugated to antibodies having determinants on cells for which therapeutic growth control is desired may be used to direct TGF-β into the cell. Such TGF-β:TGF-β receptor:antibody complexes may be particularly useful in the inhibition of growth in cancer cells that express few if any TGF-β receptors or have somehow lost the ability to respond to the growth-restraining actions of TGF-β.

Knowledge of the type III TGF-β receptor structure may be useful in designing synthetic TGF-β analogues which are capable of inducing the biological effects of the TGF-βs. Moreover, knowledge of TGF-β receptor biology may contribute significantly to understanding the normal growth regulation process, how defects in the process result in unrestrained proliferation in neoplastic cells, and what actions may correct or override these defects and restore normal growth regulatory mechanisms.

Effective methods for controlling the effects of TGF-β on cells expressing TGF-β receptors may include obstructing access to the functional domain of the receptor with receptor-agonists or neutralizing antibodies so that signal induction of TGF-β via the ligand receptor complex is prevented. In this way, the natural ligand, TGF-β, would find fewer receptors available for binding resulting in mitigated signal induction.

Purified type III TGF-β receptors may also find use in the isolation of the TGF-βs and other novel growth factors related to the TGF-β family.

The various aspects of the method of the invention are described in more detail in the subsections below and in the examples which follow.

5.1. IDENTIFICATION OF THE NORMAL GROWTH REGULATORY RECEPTOR FOR TGF-β

In accordance with the invention, a source of TGF-β receptor should be identified before proceeding with purification, structural characterization, and the molecular cloning and expression of a TGF-β receptor gene. The invention is directed to the type III receptor for TGF-β and should be distinguished from other receptor classes which may also be present on the surface of some cells.

A normal human embryonic cell line, HEPM, was used as a source of the type III receptor for TGF-β. The HEPM cell line was initially derived from the secondary palatal mesenchyme of a human abortus toward the end of the embryonic phase of development, about 50 to 60 days into gestation (Voneda and Pratt, 1981, J. Craniofac. Genet. Dev. Biol. 1:411–423). HEPM cells have the normal diploid karyotype of a female embryo, show no chromosomal aberration by the fourteenth passage (Welsch et al., 1986, Teratogenesis Carcinog. Mutagen. 6:383–392), and presumably represent the undifferentiated fibroblast-like cells from the palatal shelves. The gestational age of these cells suggests that binding of TGF-β to HEPM cell receptors may initiate a growth stimulatory response. The cell line has been used in the study of regulatory events associated with the development of cleft palate during midgestation (Kim et al., 1984, J. Histochem. Cytochem. 32:1234–1237).

The HEPM cell line was chosen as a source for TGF-β receptor because these cells were found to contain more TGF-β receptors per cell than any other cell line tested. However, the method of the invention is in no way limited to the use of HEPM cells as a source of TGF-β receptors since many, if not most cells express TGF-β receptors.

The presence of receptors specific for TGF-β on HEPM cells may be determined by measuring biological responses to treatment with exogenous TGF-β1, and TGF-β2. Utilizing the assays described in Section 6, infra, applicants determined that both TGF-β1 and TGF-β2 stimulate DNA synthesis and growth in HEPM cells to a similar degree, suggesting that both factors bind to the same receptor. Competitive binding studies, such as those described in Section 6.2.2, infra, may be used to determine whether these observed biological responses involve binding to a TGF-β-specific receptor or to some other growth factor receptor. In this regard, applicants have determined that the epidermal growth factor and TGF-β exert their biological effects through interactions with distinct receptors and that a synergistic effect on cell proliferation is obtained when both growth factors are used to stimulate HEPM cell growth.

The binding affinity of HEPM cell-surface receptors specific for TGF-β may be measured by utilizing the radioreceptor assay described in Section 6.1.4., infra, Applicants' discovery that binding of TGF-β to HEPM cells is saturable is consistent with previous studies (Wakefield et al., 1987, J. Cell. Biol. 105:965–975). The relationship between saturable binding and receptors specific for TGF-β may be analyzed by the method of Scatchard (Scatchard, et al., 1949, Ann. NY Acad. Sci. 51:660–672). Using this analytical technique, applicants determined that HEPM cells express a low capacity, high affinity binding site for TGF-β with a dissociation constant of 58 pM. In addition, these cells also contain a second, high capacity, low affinity binding site with a dissociation constant of 898 pM.

Once a cell line having functional receptors for TGF-β has been identified and characterized for its ability to bind ligand, the purification methods of the invention may be utilized to isolate homogeneous type III TGF-β receptor.

5.2. PURIFICATION OF TYPE III TGF-β RECEPTOR

In accordance with the method of the invention, type III TGF-β receptors may be purified to homogeneity from any cell line or tissue having such receptors. In a specific embodiment, human embryonic cells (HEPM cells) were used as the source of receptor since receptors specific for both TGF-β1, and TGF-β2 are expressed on these cells in high numbers (about 287,000 sites per cell, 95% of which are type III receptors).

The type III receptor for TGF-β may be purified by utilizing various procedures and techniques known in the art, including but not limited to chromatography, centrifugation, electrophoresis, differential solubility, or by any other standard technique for the purification of proteins. In a specific embodiment, the type III TGF-β receptor was purified by affinity chromatography. Specifically, recombinant TGF-β1, was immobilized onto polymeric resin and used to isolate receptors from a solution containing solubilized HEPM cell membranes as described in Section 7, infra. Recombinant TGF-β1, was obtained in accordance with the method disclosed in U. S. patent application Ser. No. 189,984, which is incorporated by reference herein in its entirety. The invention is not limited to the use of TGF-β1 in the affinity purification of type III TGF-β receptors as TGF-β2, which also binds HEPM cell surface receptors for TGF-β, may also be used. Likewise, other ligands or antibodies capable of binding TGF-β receptor may be employed in conjunction with affinity chromatography techniques to isolate the TGF-β receptor of the invention. Affinity purified receptors may be assayed for their ability to bind ligand as described in Section 7.2., infra.

Once the purified TGF-β receptor of the invention has been obtained, techniques known in the art for determining all or part of its primary structure may be used so that oligonucleotide probes corresponding to specific regions of the amino acid sequence may be designed, constructed and employed in the molecular cloning of TGF-β receptor gene.

5.3. PRODUCTION OF THE TYPE III TGF-β RECEPTOR

The type III TGF-β receptor of the invention may be produced in large quantities by various methods known in the art including but not limited to isolation from large scale culture or fermentation of HEPM cells, other cells naturally expressing the receptor, or recombinant host organisms which direct the synthesis, expression and processing of biologically active type III TGF-β receptor. Alternatively, the type III TGF-β receptor may be chemically synthesized in whole or in part by methods well known in the art, including the solid phase peptide synthesis technique. Purification of homogeneous type III TGF-β receptor may be accomplished by employing the methods described in Section 7, infra, or by other methods known in the art for the purification of proteins.

5.4. MOLECULAR CLONING AND EXPRESSION OF TYPE III TGF-β RECEPTOR GENE

In the practice of the method of the invention, the nucleotide coding sequence for type III TGF-β receptor, or its functional equivalent, can be used to generate recombinant molecules which will direct the expression of the type III TGF-β receptor product. The nucleotide coding sequence for the receptor may be obtained from cells expressing type III TGF-β receptors. For example, the HEPM cell line may be used as the source of the nucleotide coding sequence. The coding sequence may be obtained by cDNA cloning of RNA isolated and purified from such cellular sources or by genomic cloning. Either cDNA or genomic libraries of clones may be prepared from the DNA fragments generated using techniques known in the art, including but not limited to the use of restriction enzymes.

The fragments which contain the gene for type III TGF-β receptor may be identified in a number of ways known in the art. For example, a portion of the receptor amino acid sequence can be used to deduce the DNA sequence, which DNA sequence can then be chemically synthesized, radioactively labeled, and used as a hybridization probe.

Other methods which can be used to isolate the type III TGF-β receptor gene include but are not limited to chemically synthesizing the gene sequence itself from a known sequence which may, for example, be derived from the amino acid sequence of receptor. Alternatively, in vitro translation of selected mRNA followed by functional or immunological assays of the translation products can be used. The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. Recombinant molecules can be introduced into host cells via transformation, transfection, infection, electroporation, etc.

In a particular embodiment, the type III TGF-β receptor gene may may be cloned by taking advantage of the inducible down-regulation of receptors in HEPM source cells. In this regard, applicants have determined that significant down-regulation of the type III TGF-β receptors on HEPM cells can be achieved by treating these cells with TGF-β for 18 hours (Section 6.3.1., infra). It is possible that this observed down-regulation is a reflection of a corresponding reduction in the synthesis of fully processed receptor mRNA. Thus, differences in the levels of receptor mRNA in treated and untreated cells may, for example, be used in conjunction with subtractive cloning techniques well known in the art to enhance the probability of cloning a type III receptor gene sequence.

Due to the inherent degeneracy of nucleotide coding sequences, other DNA sequences which encode substantially the same or a functionally equivalent amino acid sequence may be used in the practice of the present invention for the cloning of the type III TGF-β receptor.

Such alterations of the receptor nucleotide sequence include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

5.4.1. CONSTRUCTION OF EXPRESSION VECTORS CONTAINING THE TYPE III TGF-β RECEPTOR CODING SEQUENCE

In order to express a biologically active, mature form of the type III TGF-β receptor, an expression vector/host system should be chosen which provides not only for high levels of transcription and translation but for the correct processing of the gene product. In a particular embodiment a mammalian host cell system may be used so that the product is correctly processed and secreted into the extracellular environment.

A variety of animal/host expression vector system (i.e., vectors which contain the necessary elements for directing the replication, transcription and translation of the receptor coding sequence in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionine promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionien promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire receptor gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the receptor coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the receptor gene and appropriate transcriptional/translational control signals. These methods may include in vitro recombinant DNA techniques, synthetic techniques and in vivo recombinations (genetic recombination).

For example, in cases where an adenovirus is used as an expression vector, the receptor coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing TGF-β receptor in infected hosts. Similarly, the vaccinia 7.5K promoter may be used.

An alternative expression system which could be used to express receptor is an insect system. In one such system, *Autographa californica* nuclear polyhedrosis virus (AcNPV) is used as a vector to express foreign genes. The virus grows in *Spodoptera frugiperda* cells. The receptor coding sequence may be cloned into nonessential regions (for example the polyhedrin gene) of the virus and placed under control of an AcNPV promoter (for example the polyhedrin promoter). Successful insertion of the receptor coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters). Therefore, expression of the genetically engineered receptor may be controlled. This is important if the protein product of the cloned foreign gene is lethal to host cells. Furthermore, modifications (e.g. glycosylation) and processing (e.g., cleavage) of protein products are important for the function of the protein. Different host cells have characteristic and specific mechanisms for the post-translational processing and modificatin of proteins. Appropriate cell lines or host systems can be chosen to ensure the correct modification and processing of the foreign protein expressed.

5.4.2. IDENTIFICATION OF TRANSFECTANTS OR TRANSFORMANTS EXPRESSING THE TYPE III TGF-β RECEPTOR GENE PRODUCT

The host cells which contain the recombinant type III TGF-β receptor coding sequence and which express the biologically active, mature product may be identified by at least four general approaches: (a) DNA-DNA hybridization; (b) the presence or absence of "marker" gene functions; (c) assessing the level of transcription as measured by the expression of receptor mRNA transcripts in the host cell; and (d) detection of the mature gene product as measured by ligand binding ability, immunoassay and, ultimately, by its biological activity.

In the first approach, the presence of the receptor coding sequence inserted in the expression vector can be detected by DNA-DNA hybridization using probes comprising nucleotide sequences that are homologous to the receptor coding sequence.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the receptor coding sequence is inserted within a marker gene sequence of the vector, recombinants containing the receptor coding sequence can be identified by the absence of the marker gene function. Alternatively, a marker gene can be placed in tandem with the receptor sequence under the control of the same or different promoter used to control the expression of the receptor coding sequence. Expression of the marker in response to induction or selection indicates expression of the receptor coding sequence.

In the third approach, transcriptional activity for the receptor coding region can be assessed by hybridization assays. For example, polyadenylated RNA can be isolated and analyzed by Northern blot using a probe homologous to the receptor coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as radioimmunoprecipitation, enzyme-linked immunoassays and the like. The ultimate test of the success of the expression system, however, involves the detection of the biologically active type III TGF-$\beta$ receptor gene product. Where the host cell secretes the gene product the cell free media obtained from the cultured transfectant host cell may be assayed for receptor activity. Where the gene product is not secreted, cell lysates may be assayed for such activity. Assays such as the binding assays described herein or the like may be used.

Once a clone that produces high levels of biologically active, mature type III TGF-$\beta$ receptor is identified, the clone may be expanded and receptor may be purified as described herein or by using techniques well known in the art. Such methods include affinity purification, chromatographic methods including high performance liquid chromatography, and the like.

6. EXAMPLE: IDENTIFICATION AND CHARACTERIZATION OF THE TGF-$\beta$ RECEPTOR ON HEPM CELLS In the example which follows, a human embryonic cell line, HEPM, was identified as an excellent source for the isolation of the type III TGF-$\beta$ receptor. Various characteristics and properties of the HEPM cell surface receptors for TGF-$\beta$ are described herein.

6.1. MATERIALS AND METHODS

6.1.1. GROWTH STIMULATION ASSAYS

HEPM cells (5,000 cells/50 $\mu$l) were subcultured in 96-well tissue culture plates (Falcon 30072) in growth medium comprising minimal essential medium (Gibco, Grand Island, N.Y.) supplemented with 10% heat-inactivated fetal bovine serum, 600 $\mu$g/ml L-glutamine, 500 $\mu$g/ml penicillin and 500 $\mu$g/ml streptomycin for a 24-hour period at 37° C. in a humidified 5% $CO_2$/95% air atosphere. A nondividing, quiescent state of growth was achieved by subsequent incubation for 48 hours in growth medium supplemented with 0.5% fetal bovine serum. Quiescent cells were then stimulated to proliferate by the addition of fetal bovine serum (10 $\mu$l) and test samples of TGF-$\beta$1, or TGF-$\beta$2 (50 $\mu$l). The cells were incubated an additional 66 hours at 37° C. At the end of this incubation period each well received 50 $\mu$l of growth medium containing 0.1 $\mu$Ci 5-[$^{125}$I] iodo-2'-deoxyuridine (Amersham, Arlington Heights, Ill.) and cells were allowed to incubate an additional 6 hours at 37° C. The monolayers were washed with phosphate-buffered saline (PBS), fixed in 95% methanol, and air dried. The radionuclide incorporated by the cells was solubilized with 200 $\mu$l of 1N sodium hydroxide. The amount of cell growth was measured by the amount of radionuclide incorporated into the DNA of actively growing cells.

Alternatively, growth stimulation in monolayer was monitored by cell counting. Cell monolayers were washed with PBS and then treated with 100 $\mu$l 0.25% trypsin solution at 37° C. until cells became detached from the culture surface. Fetal bovine serum (100 $\mu$l) was then added to each well to inhibit further action by trypsin. The resulting cell suspension was counted by the standard hemacytometer method. The viability of cells, greater than 98% in these examples, was determined by trypan blue dye-exclusion.

6.1.2. STIMULATION OF ANCHORAGE INDEPENDENT GROWTH ASSAY

A 0.5 ml base layer of 0.5% agar (Agar Noble; Difco Laboratories, Detroit, Mich.) in growth medium was added to 24-well Costar tissue culture plates 0.5 ml 0.3% agar in growth medium containing $1 \times 10^4$ HEPM cells and various concentrations of TGF-$\beta$ or other test samples was overlaid on the base layer of agar in triplicate wells. The plates were incubated at 37° C. in a humidifed atmosphere of 5% $CO_2$ in air for up to 14 days without refeeding. Colonies were enumerated unfixed and unstained. The number of colonies with more than 6 cells were scored.

6.1.3. CO-STIMULATION WITH EGF ASSAY

Quiescent HEPM cells were stimulated to proliferate by the addition of fetal bovine serum (15 $\mu$) and test samples of TGF-$\beta$2 (50 $\mu$l) and/or EGF (50 $\mu$l), resulting in a total assay volume of 165 $\mu$l. The amount of cell growth was measured by the amount of radionuclide incorporated into the DNA of actively growing cells.

6.1.4. RADIORECEPTOR ASSAY

HEPM cells were grown to confluence ($1 \times 10^5$ cells/well) in 24-well Costar tissue culture plates. Prior to the binding assay, cells were pre-incubated in serum-free growth medium at 37° C. for 4 hours to allow for the dissociation of TGF-$\beta$ from occupied cells surface receptors. The resulting monolayers were washed 2 times in binding buffer (Dulbecco's MEM+0.1% BSA+25 mM HEPES). 250 $\mu$l of binding buffer containing 0.5 $\mu$g/ml [$^{125}$I]-iodoTGF-$\beta$1, (specific activity of 100 $\mu$Ci/$\mu$g) together with increasing amounts of unlabeled TGF-$\beta$1 were added to duplicate wells. Steady state binding was carried out at 4° C. for 3 hours. After incubation cells were washed 3 times with cold binding buffer and solubilized in 200 $\mu$l of Triton solution (20 mM HEPES, 1% Triton X-100, 10% glycerol, 0.01% BSA, pH 7.4). Radioactivity was determined using a gamma spectrometer. Non-specific binding was determined in the presence of a 1,000-fold molar excess unlabeled TGF-$\beta$1.

6.1.5. AFFINITY LABELING OF TGF-$\beta$ CELL SURFACE RECEPTORS

Confluent monolayers of HEPM cells ($1 \times 10^5$ cell/well) grown in 24-well tissue culture plates (Costar) were washed twice with binding buffer and incubated with 1.0 mL of the same buffer at 37° C. for 1.5 hours to dissociate any TGF-$\beta$ bound to cell surface receptors. The buffer was discarded and the monolayers were incubated at 4° C. for 3 hours with 250 $\mu$l of binding buffer containing 50 ng/mL of [$^{125}$I]-iodo-TGF-$\beta$ (specific activity of 1000 $\mu$Ci/$\mu$g) in the presence or absence of 1000 ng/mL or unlabeled TGF-$\beta$. The monolayers were then washed three times with ice-cold binding buffer and incubated for 15 minutes at 4° C. in the presence of 0.5 mL of binding buffer to which 5 μl of 25 mM DSS (disuccinimidyl suberate, Pierce) in DMSO (dimethyl sulfoxide) were added. At the end of this incubation, the monolayers were washed once with a solution of 10 mM Tris, 1 mM EDTA in PBS pH 7.4 to quench the unreacted DSS. The monolayers were solubilized with 100 μl of 1% v/v Triton X-100, 10 mM Tris, 1 mM EDTA, pH 7.0 for 5 minutes at room temperature and the detergent insoluble material was separated by centrifugation at 12,000 xg. The detergent soluble material was immediately processed or frozen at −70° C.

6.2. BIOLOGICAL RESPONSE MEDIATED BY THE TGF-β RECEPTOR

6.2.1. PROLIFERATIVE RESPONSE

The effect of TGF-β on the growth of HEPM cells was deterined by the growth stimulation assays described in Materials and Methods.

Radiolabeled cells were exposed to increasing amounts of TGF-β1, or TGF-β2. The results are presented in FIG. 1a and FIG. 1b, respectively. Both TGF-β1, and TGF-β2 demonstrated similar potencies in stimulating the proliferation of HEPM cells ($ED_{50}$ of 5pM and 2.3 pM, respectively). The results suggest that the action of TGF-β1, and TGF-β2 on HEPM cells is mediated by a single TGF-β receptor.

The proliferative response of HEPM cells to TGF-β treatment as measured by cell counting also implicates a growth factor/receptor-mediated process. Cultures of HEPM cells treated with 50 pM of TGF-β1, reached a cell density twice that observed in untreated cultures by 96 hours post-treatment.

6.2.2. SYNERGISM OF EGF IN THE TGF-β/TGF-β RECEPTOR SYSTEM

The response of HEPM cells to TGF-β treatment in the presence of EGF was determined by radiolabeling the DNA of dividing cells as described in Materials and Methods. A suboptimal dose of TGF-β2 was analyzed for growth stimulatory activity in the presence of EGF. HEPM cells treated with 13 ng/ml EGF alone resulted in a 21% stimulation and with 0.3 ng/ml TGF-β2 alone resulted in a 150% stimulation. HEPM cells treated with both EGF and TGF-β2 at the same doses gave a 511% stimulation, a potentiated response of 340% over that expected from the sum of the two individual responses. The observed synergy between EGF and TGF-β2 indicates that each growth factor stimulates HEPM proliferation via distinct mechanisms; that is, TGF-β action is not mediated directly through the EGF receptor but through a TGF-β-specific receptor.

6.3. PROPERTIES OF HEPM CELL-SURFACE RECEPTORS FOR TGF-β

6.3.1. DETERMINATION OF RECEPTOR NUMBER AND AFFINITY

The radioreceptor assay described in Materials and Methods was used to characterize the affinity and number of cell-surface receptors for TGF-β on HEPM cells. Specific binding of [$^{125}$I]-iodo-TGF-β in these assays was 20% of the total radioligand present. Competition between iodinated TGF-β and unlabeled TGF-β for binding to HEPM cells indicated that binding is saturable and competed by unlabeled ligand (FIG. 4A,4B). Half-maximal displacement of radioligand occurred at 100 pM (2.6 ng/ml) unlabeled TGF-β1. Competitive binding data were plotted according to the method of Scatchard (Scatchard, et al., 1947, Ann. NY Acad Sci 51:660–672) and the results are presented in FIG. 5. A distinctly curvilinear isotherm was obtained indicating the presence of at least two classes of binding sites on HEPM cells. Scatchard plots analyzed by the two-site model demonstrate that the binding detected corresponds to a high-affinity site with a kd of 58 pM and a low-affinity site with a kd of 898 pM. Quantitative analysis determined that HEPM cells contain a total of 287,000 TGF-β receptors per cell (55,400 high affinity and 231,600 low affinity sites). These results show that the saturable binding of TGF-β1, is due to the presence of high numbers of TGF-β1, cell-surface receptors.

HEPM cells treated for 18 hours with 100 pM recombinant TGF-β1, exhibited substantial TGF-β receptor down-regulation. Briefly, HEPM cells were treated with 100pM TGF-β1, for 18 hours, washed with serum-free medium, and incubated in fresh serum-free medium for 60 minutes to allow for the disassociation of residually bound TGF-β1. The radioreceptor assay described in Materials and Methods was used to assess the extent of receptor down-regulation in the treated cells relative to untreated control cells. The results indicate that treated cells express fewer high affinity (kd of 40 pM) and low affinity (kd of 974 pM) binding sites. A 74% down-regulation of the high affinity binding sites was observed (14,000 sites/cell in treated cells compared to 55,400 sites/cell in control cells). Similarly, a 53% down-regulation of the low affinity binding sites was observed (108,800 sites/cell in treated cells compared to 231,600 sites/cell in control cells). The combined total receptor down-regulation observed was 57%.

6.3.2. RELATIONSHIP BETWEEN RECEPTOR OCCUPANCY AND BIOLOGICAL RESPONSE

In order to determine the quantitative relationship between receptor occupancy and receptor-mediated biological response, TGF-β-induced growth stimulation and receptor binding at variable concentrations of TGF-β were compared. The comparison of these two parameters is presented in FIG. 6. Interestingly, the concentration of ligand necessary to occupy all of the TGF-β receptor sites on HEPM cells is about 20 times the concentration required to generate the maximal growth stimulatory response. The excess amount of TGF-β receptors expressed on the surface of HEPM cells, a total of about $2.3 \times 10^5$ receptors per cell, make these cells an ideal source for the isolation and purification of TGF-β receptors.

6.3.3. IDENTIFICATION OF TGF-β RECEPTORS ON HEPM CELLS

Figure 7:
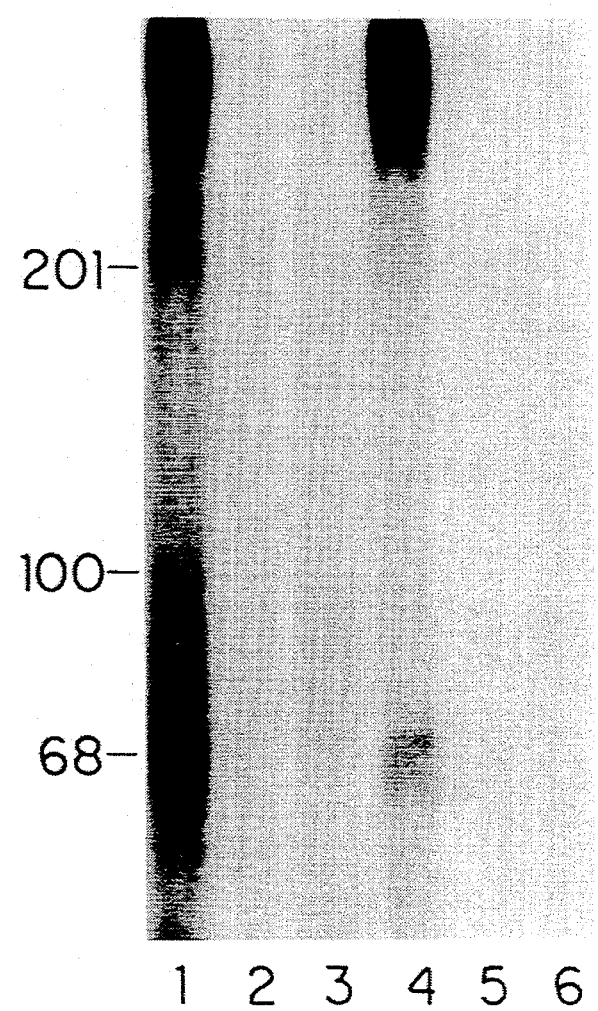

HEPM cell surface receptors affinity labeled with [$^{125}$I]-iodo-TGF-β and analyzed under reducing conditions on SDS-PAGE migrated into three distinct bands with the large majority of signal localized in the high molecular weight band seen in FIG. 7, which likely corresponds to a type III receptor specific for TGF-β having a molecular mass of about 240–260 kd. Minor receptor species are apparent at about 150 kd and 68–85 kd in FIG. 7, both of which demonstrate a lower degree of affinity for TGF-β.

7. EXAMPLE: PURIFICATION OF TYPE III TGF-β RECEPTOR

The following example describes the affinity purification of the type III TGF-β receptor from HEPM cells. The purified receptor thus obtained was characterized functionally and structurally.

7.1. MATERIALS AND METHODS

7.1.1. PREPARATION AND SOLUBILIZATION OF MEMBRANES

HEPM cells were grown to confluence in tissue culture flasks, T150 (Costar), or roller bottles, 850 cm² (Costar), in minimal essential medium (MEM, Gibco, Grand Island, N.Y.) supplemented with 10% heat inactivated fetal bovine serum (BIOCEL), 600 μg/ml L-glutamine, 500 μg/ml penicillin and 500 μg/ml streptomycin in a humidified 5% $CO_2$, 95% air at 37° C. controlled atmosphere, or $CO_2$ atmosphere at 37° C. (warm room, roller bottles) rotating at 5–7 revolutions per minute. The confluent monolayers were washed twice with PBS and incubated for 48 hours in fresh growth media without fetal bovine serum in the above-described growth conditions. The monolayers were again washed with ice-cold PBS and the cells were solubilized for 5 minutes at room teperature with a solution containing 1% Triton X-100, 25 mM Hepes pH 7.4. The detergent soluble material was separated from the insoluble material by centrifugation at 12,000 xg. The detergent soluble material was collected and processed immediately or frozen at −70° C.

7.1.2. IMMOBILIZATION OF TGF-β TO SOLID SUPPORT

TGF-β samples purified to homogeneity by reverse phase HPLC (Gentry, et al., 1988, Mol. Cell. Biol. 8:4162) were reduced to half the original volume by vacuum under centrifugation (SpeedVac) to eliminate the acetonitrile. The volume was determined and the solution was adjusted to 0.1M sodium phosphate (using a 1:10 dilution of 1M sodium phosphate stock pH 7.5), 100 mM NaCl (using a stock of 1M NaCl). One milliliter Affi-Gel 10 resin (BioRad) previously washed with ice cold $H_2O$ was incubated with the adjusted TGF-β solution at 4° C. overnight with end-over-end mixing. The resin was extensively washed with a solution containing 1% Triton X-100, 25 mM Hepes pH 7.4, 100 mM NaCl, and stored at 4° C.

About 2 ml of HPLC-purified recombinant TGF-β1 at a concentration of 250 μg/ml was coupled to 1 ml of packed Affi-Gel-10 beads using this procedure.

7.1.3. AFFINITY LABELING OF SOLUBLE TGF-β RECEPTORS

Solubilized receptor samples (50 μl) were diluted with three volumes of binding buffer containing 0.5% v/v Triton X-100 and 50 ng/ml [$^{125}$I]-iodo-TGF-β. The samples were incubated at 4° C. for 3 hours in the presence or absence of 1,000 ng/ml unlabeled TGF-β. Four microliters (4 μl) of 10 mM DSS in DMSO were then added. After 15 minutes the unreacted DSS was quenched by adding 20 μl of 100 mM Tris/HCl pH 7.0.

Affinity-labeled samples were incubated at 4° C. for 2 hours with 15 μl of packed WGA-sepharose beads (wheat germ aglutinin-sepharose, Sigma) with end-over-end mixing. The beads were sedimented by centrifugation at 12,000 xg for 1 minute and washed three times with a buffer solution containing 0.5% v/v Triton X-100, 10 mM Tris/HCl, mM EDTA. The washed, packed beads were heated for 5 minutes at 95° C. in the presence of 20 μl of electrophoresis sample buffer containing 5% 2-mercaptoethanol. The supernatants were retained for SDS-PAGE analysis.

7.1.4. SDS-PAGE AND AUTORADIOGRAPHY

SDS-PAGE was performed as described (Laemmli, 1970, Nature 227:680–685) using a 6.25% or 7.5% slab gel and a 5% stacking gel. All samples containined 5% 2-mercaptoethanol. After electrophoresis, the gels were stained for protein with Coomassie brilliant blue R250 (Serva) and dried on filter paper (Whatman, no. 5) for autoradiography. The molecular weight markers used were purchased from Sigma (carbonic anhydrase, 29 Kd; ovalbumin, 45 Kd; phosphorylase B, 97.4 Kd; β galactosidase, 116 Kd; myosin 205 Kd). Kodak XAR autoradiography film and DuPont Cronex Plus enhancing screens were used.

7.1.5. AFFINITY CHROMATOGRAPHY

Approximately 150 ml solubilized HEPM membranes were incubated at 4° C. with 500 μg TGF-β1, coupled to 1 ml Affi-Gel beads for 3 hours with end-over-end mixing. The beads were recovered by centrifugation at 12,000 xg, packed in a 10 ml column, and the packed column washed with 15 ml ice-cold solution containing 1% Triton X-100, 25 mMHepes, pH 7.4. TGF-β receptor was eluted with 5 ml of solution containing 25mM sodium phosphate, 1% Triton X-100, pH 4.0; 1 ml fractions were collected.

7.2. CHARACTERIZATION OF AFFINITY PURIFIED TYPE III TGF-β RECEPTOR

7.2.1. ELECTROPHORETIC ANALYSIS

Affinity purified samples were adjusted to pH 7.4 with 1M NaOH and 20 μl of WGA-Sepharose was added and mixed end-over-end for 2 hours at 4° C. The tubes were then spun at 12,000 xg for 1 minute to sediment the beads, the supernatant was removed and 20 μl of electrophoresis sample buffer was added to the beads and incubated at room temperature for 30 minutes. FIG. 9 shows the mobility of the purified TGF-β receptor on a 6.25% SDS-PAGE under reducing conditions using a 5% stacking gel. There is only one Coomassie stainable band, almost comigrating with the myocin marker, at a calculated molecular mass of 200–206 Kd. The lack of any other bands indicates the specificity of TGF-β complex as analyzed by crosslinking and SDS-PAGE analysis under identical conditions (FIG. 7 and FIG. 10).

7.2.2. BINDING CAPACITY

Aliquots of the affinity purified receptor preparations and radiolabeled TGF-β1 were allowed to bind and were cross-linked with DSS as described in Section 7.1.3., supra. The results presented in FIG. 10 demonstrate that the purified receptors of the invention specifically bind TGF-β.

7.2.3. AMINO ACID COMPOSITION AND SEQUENCING

Affinity purified samples were electrophoresed as described in Section 7.1.4, supra. Electrophoresed samples were transferred to Immobilon (Millipore) membranes as described (Matsudaira, 1987, J. Biol. Chem. 262: 10035–10038) and stained with Coomassie. Stained bands correponding to the type III TGF-$\beta$ receptor were excised and subjected to amino acid composition and sequencing analysis.

Amino acid composition analysis was performed on an automated amino acid analyzer (ABI model) and amino acids were detected as their PITC derivatives. Table I shows the amino acid composition for the type III TGF-$\beta$ receptor purified from HEPM cells.

TABLE I

AMINO ACID COMPOSITION OF AFFINITY PURIFIED TYPE III TGF-$\beta$ RECEPTOR[1]

| Amino Acid[2] | pMoles A. A. | Mole % M/100 M | Residues nG A.A. Per Mole | Residues Per Mole | Integer Res/Mol |
|---|---|---|---|---|---|
| ASx | 266.00 | 11.55 | 12424 | 107.96 | 108 |
| GLx | 160.00 | 6.95 | 8384 | 64.94 | 65 |
| SER | 165.00 | 7.16 | 5831 | 66.96 | 67 |
| GLY | 279.00 | 12.11 | 6460 | 113.23 | 113 |
| HIS | 54.00 | 2.34 | 3006 | 21.92 | 22 |
| ARG | 155.00 | 6.73 | 9825 | 62.91 | 63 |
| THR | 91.00 | 3.95 | 3734 | 36.93 | 37 |
| ALA | 240.00 | 10.42 | 6923 | 97.40 | 97 |
| PRO | 112.00 | 4.86 | 4414 | 45.45 | 45 |
| TYR | 87.00 | 3.78 | 5762 | 35.31 | 35 |
| VAL | 146.00 | 6.34 | 5874 | 59.25 | 59 |
| MET | 0.00 | 0.00 | 0 | 0.00 | 0 |
| ILE | 77.00 | 3.34 | 3536 | 31.25 | 31 |
| LEU | 221.00 | 9.60 | 10150 | 89.69 | 90 |
| PHE | 87.00 | 3.78 | 5197 | 35.31 | 35 |
| LYS | 163.00 | 7.08 | 8479 | 66.15 | 66 |
| TOTAL | 2303.00 | 100.00 | 100000 | 934.66 | 933 |

[1]A molecular weight assumption of 100 Kd was used in these calculations.
[2]Cystein and tryptophan residues not determined.

The first 7 amino-terminal amino acids of the type III TGF-$\beta$ receptor were determined through analysis performed in a automated gas phase sequencer (ABI model 470). The assigned amino acids are:

NH$_2$-Lys-Tyr-Tyr-Asp-Lys-Asp-Tyr

What is claimed is:

1. A protein that:
   (a) has an amino-terminal amino acid sequence comprising:

NH$_2$-Lys-Tyr-Tyr-Asp-Lys-Asp-Tyr;

(b) has a glycosylated apparent molecular weight by gel electrophoresis under reducing conditions of about 200,000 to about 206,000 daltons;
   (c) may be obtained from a naturally occurring mammalian fibroblast;
   (d) is a specific receptor for TGF-$\beta$; and
   (e) is free from bands due to other proteins which occur naturally in mammalian fibroblasts, when said protein is analyzed by the polyacrylamide gel electrophoresis procedure of Laemmli using Coomassie stain for protein detection.

2. A glycosylated protein of claim 1.
3. An un-glycosylated protein of claim 1.
4. The protein of claim 2 in which the TGF-$\beta$ is TGF-$\beta$1.
5. The protein of claim 4 in which the TGF-$\beta$1 is recombinant TGF-$\beta$1.
6. The protein of claim 2 in which the TGF-$\beta$ is TGF-$\beta$2.
7. The protein of claim 2 in which the TGF-$\beta$ is recombinant TGF-$\beta$2.
8. The protein of claim 5 having a dissociation constant for TGF-$\beta$1 of about $1 \times 10^{-12}$M to about $1 \times 10^{-9}$M.
9. A Type III TGF-$\beta$ receptor, obtained by the method comprising:
   (a) solubilizing membranes from cultures HEPM cells to make a solubilized HEPM membrane preparation;
   (b) covalently binding TGF-$\beta$ to a solution-permeable matrix to make a TGF-$\beta$ affinity matrix;
   (c) contacting the solubilized HEPM membrane preparation with the TGF-$\beta$ affinity matrix;
   (d) removing unbound components of the solubilized HEPM membrane preparation from the TGF-$\beta$ affinity matrix; and
   (e) eluting said Type III TGF-$\beta$ receptor from said TGF-$\beta$ affinity matrix;
   (f) has an amino-terminal amino acid sequence comprising NH$_2$-Lys-Tyr-Tyr-Asp-Lys-Asp-Tyr;

(g) has a glycosylated apparent molecular weight by gel electrophoresis under reducing conditions of about 200,000 to 260,000 daltons;
   (h) specifically binds TGF-$\beta$; and
   (i) is free from bands due to other proteins which occur naturally in mammalian fibroblasts, when said Type III TGF-$\beta$ receptor is analyzed by the polyacrylamide gel electrophoresis procedure of Laemmli using Coomassie stain for protein detection.

10. The protein of claim 9 in which the TGF-$\beta$ is TGF-$\beta$1.
11. The protein of claim 10 in which the TGF-$\beta$ is recombinant TGF-$\beta$1.
12. The protein of claim 9 in which the TGF-$\beta$ is TGF-$\beta$2.
13. The protein of claim 12 in which the TGF-$\beta$ is recombinant TGF-$\beta$2.
14. The protein of claim 11 having a dissociation constant for TGF-$\beta$1 of about $1 \times 10^{-12}$M to about $1 \times 10^{-9}$M.
15. The protein of claim 1 wherein said fibroblast is an HEPM cell.

* * * * *